United States Patent [19]

Bertolini

[11] 4,291,035

[45] Sep. 22, 1981

[54] PHARMACEUTICAL COMPOSITIONS COMPRISING TRIMETHOPRIM AND N-ETHYL-γ-PYRIDONE-3-CARBOXYLIC ACID DERIVATIVES

[75] Inventor: Alfio Bertolini, Scandiano, Italy

[73] Assignee: Sigma-Tau Industrie Farmaceutiche Riunite S.p.A., Rome, Italy

[21] Appl. No.: 56,657

[22] Filed: Jul. 11, 1979

[30] Foreign Application Priority Data

Jul. 13, 1978 [IT] Italy ............................ 50274 A/78

[51] Int. Cl.$^3$ .................. A61K 31/505; A61K 31/47; A61K 31/44
[52] U.S. Cl. .................................. 424/251; 424/258; 424/263
[58] Field of Search ............................... 424/251, 258

[56] References Cited

PUBLICATIONS

Chemical Abstracts 79:74139e (1973).
Chemical Abstracts 88:955g (1978) Abstracting Ann. Microbiol. (Paris) 1977 reference.
Chemical Abstracts 88:99266t (1978) Abstracting Ther. Hung. 1977, 25(3), 111-114 reference.

Primary Examiner—Jerome D. Goldberg
Attorney, Agent, or Firm—Ladas & Parry

[57] ABSTRACT

Pharmaceutical compositions comprising trimethoprim and a N-ethyl-γ-pyridone-3-carboxylic acid derivative, such as nalidixic, oxolinic or piromidic acid, are more effective than previously known trimethoprim-containing compositions for the treatment of infections affecting the urinary tract.

Trimethoprim and the foregoing acid derivatives unpredictably show a noticeable synergistic effect.

2 Claims, No Drawings ns4,291,035

PHARMACEUTICAL COMPOSITIONS COMPRISING TRIMETHOPRIM AND N-ETHYL-γ-PYRIDONE-3-CARBOXYLIC ACID DERIVATIVES

BACKGROUND OF THE INVENTION

1. Field of the Invention

The present invention relates to novel trimethoprim-containing pharmaceutical compositions and to the use of such compositions for the treatment of infections affecting the urinary tract. More specifically, the trimethoprim-containing composition of this invention are useful therapeutics in the treatment of acute and chronic infections of the urinary tract due to Gram-negative bacteria.

2. Description of the Prior Art

Trimethoprim, 2,4-diamino-5-(3,4,5-trimethoxybenzyl) pyrimidine, is a long since known, widely used antimicrobial agent.

Generally, trimethoprim has been used as compounded preparations with sulphamethoxazole (Co-trimoxazole). Also trimethoprim/rifampicin compositions have been described.

Recently, an increasingly severe criticism has been raised against the foregoing trimethoprim-containing compositions.

Co-trimoxazole may cause any of the side-effects typical of sulphonamides. These latter require close supervision of the patient because the onset of serious intoxication is unpredictable. As known, sulphonamide toxic effects range from relatively minor effects such as nausea, vomiting and drowsiness to serious complications, like renal complications (lumbar pain, haematuria etc.), allergic reactions (e.g. skin rashes) and even hepatitis.

The trimethoprim/rifampicin composition has been reported to produce abnormalities in liver function caused by the hepatotoxic nature of rifampicin. Alterations in kidney function and renal failure have also been reported.

SUMMARY OF THE INVENTION

It is, therefore, an object of the present invention to provide a trimethoprim-containing composition which does not have the untoward drawbacks of the prior art compositions.

More particularly, it is an object of the present invention to provide a trimethoprim-containing composition, extremely effective for treating infections of the urinary tract, which is free of sulphonamides and rifamicin-type antibiotics and, consequently, of the attendant undesirable side-effects.

In accordance with the invention, it has been found a pharmaceutical composition for treating infections of the urinary tract, comprising (a) an effective amount of trimethoprim, (b) an effective amount of a N-ethyl-γ-pyridone-3 carboxylic acid derivative, and (c) an inert excipient therefor.

Preferably, the N-ethyl-γ-pyridone-3-carboxylic acid derivative is selected from the group comprising nalidixic acid, oxolinic acid, piromidic acid, their pharmaceutically acceptable salts, amides and esters, and mixtures thereof (briefly referred to hereinbelow acid derivatives A).

It has been found that the compositions of the present invention have a powerful synergistic effect, as shown in details in the "Experimental investigations" section of this application. This synergism was totally unpredictable on the grounds of the previously known characteristics of trimethoprim on one hand, and nalidixic, oxolinic and piromidic acid on the other hand.

DESCRIPTION OF THE PREFERRED EMBODIMENTS

It has been found the weight ratio of trimethoprim to nalidixic, oxolinic and piromidic acid should range between 1:2 and 1:10.

Preferably, the weight ratio is 1:5.

In actual practice, the compositions of the present invention are given orally or parenterally, in any of the usual pharmaceutical forms which are prepared with conventional procedures. These forms include solid and liquid oral unit dosage forms, such as tablets, capsules, suspensions, solutions, syrups and the like as well as saline solutions for in injectable vials or bottles for phleboclysis under conditions of absolute asepticity for administration by the parenteral route.

Preferably, an orally administrable, pharmaceutical composition in unit dosage form for treating infections of the urinary tract, comprises:

(a) from 45 to 200 mg of trimethoprim;

(b) from 200 to 1000 mg of oxolinic, nalidixic or piromidic acid; and (c) an effective amount of an inert excipient therefor.

The dose which is administered will be determined by the attending physician having regard to the age, weight and condition of the patient, using sound professional judgment.

It has been found, however, that, whereas the trimethoprim dose to be administered is from 2 to 8, preferably 4–6, mg/kg/die, the dose of oxolinic acid is 10–40 mg/kg/die, and the dose of nalidixic acid and piromidic acid is 20–80 mg/kg/die.

EXPERIMENTAL INVESTIGATIONS (1) Determination of synergic effect "in vitro"

A study carried out to prove the existence of a synergic interaction between trimethoprim and the acids of class (A) gave extremely positive results. In fact, it was possible to show a super-additive effect against most of the strain tested.

The experimental work, consisting in the determination of FIC (Fractional Inhibitory Concentration, see S. R. M. Bushby and G. H. Hitchings, Trimethoprim, a sulphonamide potentiator, Br, J. Pharmac. Chemoter. (1968) 33, 72–90) in solid medium for the single anti-bacterials (i.e. the acids of class (A)) and the various compositions was carried out by using 20 strains for each genus of bacteria.

In Table 1 there are concisely shown the results obtained, expressed as percentages of strains against which the compositions of this invention exhibit a synergic effect. A value of FIC less than 1 has been regarded as evidence of a synergic effect.

It should be noted that there are no significant differences among the various compositions of the present invention, as shown by the percentage range illustrated in Table 1. All the tested compositions contained trimethoprim and either one of the N-ethyl-γ-pyridone-3 carboxylic acid derivatives at a weight ratio of 1:5.

In Table 2, the results obtained with the trimethoprim/oxolinic acid composition toward 126 clinically isolated bacteria strains are shown.

(2) Studies on resistance development toward nalidixic acid, oxolinic acid and piromidic acid, either alone or in combination with trimethoprim The experimental work was carried out by using the sub-culture technique, i.e. the culture grown in the presence of the highest drug concentration on Clark-Lubs agar plates was used as inoculum in the subsequent sensibility determination.

The rate of the resistance development in a series of bacteria strains (3Salmonella thyphimurium-3 Escherichia coli-3 Klebsiella pneumoniae-3 Proteous mirabilis) was shown to be positively affected by the compositions of the present invention. The results were substantially identical to those shown in Table 3 concerning the trimethoprim/nalidixic acid composition, for all of the tested compositions of the present invention.

In Table 4, the results obtained with the trimethoprim/oxolinic acid composition are shown.

(3) Antibacterial activity "in vivo"

A study was carried out in experimentally infected mice. The ratio of $ED_{50}$ of the N-ethyl-γ-pyridone-3-carboxylic acid derivatives to the $ED_{50}$ of the trimethoprim-containing compositions of the present invention was measured.

In Table 5 there are shown the bacteria genuses which were used for evaluating the "in vivo" antibacterial activity as well as the potentiation of the protective effect of the compositions of the present invention, wherein the trimethoprim concentration was exactly one fifth of the $ED_{50}$ exhibited by the single acids listed in (A) towards the various bacteria used for experimentally infecting the mice.

Table 5 shows that positive results were obtained against all the tested strains, without noticeable differences among the various compositions.

(4) Clinical investigations

The observations noted above were confirmed in double-blind clinical studies, by treating a number of patients suffering from infections of the urinary tract of comparable seriousness with (1) nalidixic acid, (2) oxolinic acid, (3) co-trimoxazole and (4) the compositions trimethoprim/nalidixic acid and trimethoprim/oxolinic acid of the present invention.

At the end of the treatment period (10 days), the following recovery percentages with no relapses were observed:

| | |
|---|---|
| nalidixic acid (50 mg/kg/die) | = 30% |
| oxolinic acid (25 mg/kg/die) | = 55% |
| co-trimoxazole (320 mg of trimethoprim + 1600 mg of sulfa methoxazole/die) | = 40% |
| trimethoprim/nalidixic acid | = 60% |
| trimethoprim/oxolinic acid | = 92% |

In the Tables 6 and 7, the results obtained with two compositions in accordance with the invention are shown.

TABLE 1

Potentiation of trimethoprim/nalidixic acid, trimethoprim/oxolinic acid and trimethoprim/piromidic acid compositions against 180 bacterial strains.

| Organisms | No. of strains | Percentage of synergistic effect |
|---|---|---|
| Staphylococcus | (20) | 40-60 |
| Escherichia | (20) | 60-90 |
| Salmonella | (20) | 70-90 |
| Klebsiella | (20) | 70-90 |
| Brucella | (20) | 60-80 |
| Proteus indol⁻ | (20) | 60-80 |
| Proteus indol⁺ | (20) | 50-70 |
| Pseudomonas | (20) | 10-20 |
| Streptococcus | (20) | 40-60 |

TABLE 2

Potentiation of the trimethoprim/oxolinic acid composition against 126 isolated strains.

| Organisms | No. isolated strains | F I C Index ≧1 | 0.99-0.5 | 0.49-0.25 | 0.24-0.125 |
|---|---|---|---|---|---|
| Enterococcus | 8 | 3 | 5 | | |
| Staphylococcus | 26 | 12 | 11 | 2 | 1 |
| Escherichia | 22 | 4 | 10 | 7 | 1 |
| Klebsiella | 8 | 0 | 4 | 4 | |
| Proteus indol⁺ | 9 | 2 | 6 | 1 | |
| Proteus indol⁻ | 13 | 6 | 4 | 2 | 1 |
| Pseudomonas | 10 | 5 | 3 | 2 | |
| Salmonella | 9 | 5 | 3 | | |
| Shigella | 5 | 1 | 1 | 3 | |
| Brucella | 16 | 9 | 5 | 1 | |

TABLE 3

Resistance development to nalidix acid (NA) and to a nalidixic acid/trimethoprim (NA+T) composition.

| No. of days | Minimum inhibitory concentration (μg/ml) | | | |
|---|---|---|---|---|
| | NA | NA + T | NA | NA + T |
| | Salmonella typhimurium 9 | | Escherichia coli K 12 ATCC 13762 | |
| 1 | 4 | 4 + 0.25 | 2 | 1 + 1 |
| 2 | 8 | 4 + 0.25 | 4 | 1 + 1 |
| 3 | 16 | 4 + 0.25 | 8 | 1 + 1 |
| 4 | 32 | 8 + 0.25 | 8 | 2 + 1 |
| 5 | 64 | 8 + 0.25 | 16 | 2 + 1 |
| 6 | 256 | 32 + 0.25 | 128 | 2 + 1 |
| 7 | 512 | 32 + 0.25 | 512 | 8 + 1 |
| 8 | >512 | 32 + 0.25 | >512 | 32 + 1 |
| 9 | >512 | 64 + 0.25 | >512 | 32 + 1 |
| 10 | >512 | 64 + 0.25 | >512 | 32 + 1 |
| | Klebsiella pneumoniae ATCC 10031 | | Proteus mirabilis 70 | |
| 1 | 1 | 0.5 + 1 | 4 | 1 + 5 |
| 2 | 2 | 0.5 + 1 | 4 | 1 + 5 |
| 3 | 4 | 1 + 1 | 8 | 1 + 5 |
| 4 | 4 | 1 + 1 | 8 | 4 + 5 |
| 5 | 8 | 1 + 1 | 16 | 4 + 5 |
| 6 | 8 | 2 + 1 | 32 | 4 + 5 |
| 7 | 64 | 4 + 1 | 32 | 8 + 5 |
| 8 | 256 | 16 + 1 | 128 | 16 + 5 |
| 9 | 512 | 16 + 1 | 128 | 32 + 5 |
| 10 | >512 | 16 + 1 | 256 | 32 + 5 |

TABLE 4

Resistance development to oxolinic acid (ox) and to an oxolinic acid/trimethoprim composition (ox + T).

| | Minimum inhibitory concentration (μg/ml) | | | | | | | |
|---|---|---|---|---|---|---|---|---|
| No. days | OX | OX + T | OX | OX + T | OX | OX + T | OX | OX + T |
| | Escherichia Coli 19 (") | | Escherichia Coli 6 (") | | Escherichia Freundii 15 (") | | Staphylococcus aureus Leo cc 2392 | |

TABLE 4-continued

Resistance development to oxolinic acid (ox) and to an oxolinic acid/trimethoprim composition (ox + T).

Minimum inhibitory concentration (μg/ml)

| No. days | OX | OX + T | OX | OX + T | OX | OX + T | OX | OX + T |
|---|---|---|---|---|---|---|---|---|
| 1 | 0.097 | 0.048 + 0.0081 | 0.195 | 0.048 + 0.0081 | 0.097 | 0.048 + 0.0081 | 0.39 | 0.097 + 0.0162 |
| 2 | 0.39 | 0.195 + 0.0081 | 0.39 | 0.097 + 0.0081 | 0.39 | 0.195 + 0.0081 | 0.78 | 0.195 + 0.0162 |
| 3 | 0.78 | 0.195 + 0.0081 | 0.78 | 0.195 + 0.0081 | 0.39 | 0.195 + 0.0081 | 1.56 | 0.195 + 0.0162 |
| 4 | 1.56 | 0.195 + 0.0081 | 0.78 | 0.195 + 0.0081 | 0.78 | 0.195 + 0.0081 | 1.56 | 0.195 + 0.0162 |
| 5 | 3.12 | 0.78 + 0.0081 | 0.78 | 0.195 + 0.0081 | 1.56 | 0.195 + 0.0081 | 1.56 | 0.78 + 0.0162 |
| 6 | 3.12 | 0.78 + 0.0081 | 0.78 | 0.195 + 0.0081 | 1.56 | 0.195 + 0.0081 | 3.12 | 0.78 + 0.0162 |
| 7 | 3.12 | 0.78 + 0.0081 | 0.78 | 0.195 + 0.0081 | 6.25 | 0.195 + 0.0081 | 3.12 | 0.78 + 0.0162 |
| 8 | 6.25 | 1.56 + 0.0081 | 0.78 | 0.195 + 0.0081 | 6.25 | 0.78 + 0.0081 | 6.25 | 0.78 + 0.0162 |
| 9 | 6.25 | 1.56 + 0.0081 | 3.12 | 0.78 + 0.0081 | 6.25 | 1.56 + 0.0081 | 12.5 | 0.78 + 0.0162 |
| 10 | 6.25 | 1.56 + 0.0081 | 3.12 | 1.56 + 0.0081 | 6.25 | 1.56 + 0.0081 | 12.5 | 1.56 + 0.0162 |
| | Klebsiella pneumoniae 14 (") | | Klebsiella pneumoniae 62 (") | | Proteus mirabilis 4 (") | | Enterobacter aerogeues 5 (") | |
| 1 | 0.195 | 0.097 + 0.0162 | 0.39 | 0.195 + 0.0325 | 0.39 | 0.097 + 0.0162 | 0.39 | 0.195 + 0.0325 |
| 2 | 0.78 | 0.195 + 0.0162 | 0.39 | 0.195 + 0.0325 | 0.78 | 0.195 + 0.0162 | 0.78 | 0.195 + 0.0325 |
| 3 | 1.56 | 0.195 + 0.0162 | 1.56 | 0.39 + 0.0325 | 0.78 | 0.195 + 0.0162 | 6.25 | 0.39 + 0.0325 |
| 4 | 1.56 | 0.78 + 0.0162 | 1.56 | 0.78 + 0.0325 | 1.56 | 0.195 + 0.0162 | 12.5 | 1.56 + 0.0325 |
| 5 | 3.12 | 0.78 + 0.0162 | 3.12 | 1.56 + 0.0325 | 1.56 | 0.195 + 0.0162 | 12.5 | 1.56 + 0.0325 |
| 6 | 12.5 | 0.78 + 0.0162 | 6.25 | 1.56 + 0.0325 | 3.12 | 0.195 + 0.0162 | 12.5 | 1.56 + 0.0325 |
| 7 | 12.5 | 0.78 + 0.0162 | 6.25 | 1.56 + 0.0325 | 3.12 | 0.195 + 0.0162 | 12.5 | 1.56 + 0.0325 |
| 8 | 25 | 1.56 + 0.0162 | 6.25 | 6.25 + 0.0325 | 6.25 | 0.78 + 0.0162 | 25 | 6.25 + 0.0325 |
| 9 | 25 | 6.25 + 0.0162 | 12.5 | 6.25 + 0.0325 | 6.25 | 1.56 + 0.0162 | 25 | 6.25 + 0.0325 |
| 10 | 25 | 12.5 + 0.0162 | 25 | 12.5 + 0.0325 | 12.5 | 1.56 + 0.0162 | 25 | 6.25 + 0.0325 |

(") clinically isolated strains.

TABLE 5

Potentiation of ED$_{50}$ exhibited by trimethoprim/nalidixic acid, trimethoprim/oxolinic acid and trimethoprim/piromidic acid compositions.

| Organisms | Average activity increase (n-Fold) |
|---|---|
| Escherichia coli | 4.2 |
| Klebsiella pneumoniae | 3.9 |
| Aerobacter aerogenes | 5.4 |
| Proteus mirabilis | 6.1 |
| Proteus rettgerii | 4.5 |
| Pseudomonas aeruginosa | 2.2 |

TABLE 6

Clinical evaluation of tripethoprim (4 mg/kg/day) in combination with nalidixic acid (50 mg/kg/day) in 5 patients with complicated urinary infection. Treatment duration: 10 days.

| Patients | Clinical diagnosis | Infecting organism | Outcome of therapy Bacteriologic | Clinical |
|---|---|---|---|---|
| 1 | Chronic cystitis | S. epidermidis | Eradicated | Cured |
| 2 | Chronic cystopyelitis | E. coli | Eradicated | Cured |
| 3 | Acute cystoprostatitis | P. mirabilis | Persisted | Failure |
| 4 | Chronic cystopyelitis | P. mirabilis | Persisted | Failure |
| 5 | Chronic cystopyelitis | E. coli | Eradicated | Cured |

TABLE 7

Clinical evaluation of tripethoprim (4 mg/kg/day) in combination with oxolinic acid (25 mg/kg/day) in 13 patients with complicated urinary infection. Treatment duration: 10 days.

| Patients | Clinical diagnosis | Infecting organism | Outcome of therapy Bacteriologic | Clinical |
|---|---|---|---|---|
| 1 | Pyelonephritis | Escherichia coli | Eradicated | Cured |
| 2 | Acute cystitis | Escherichia coli | Eradicated | Cured |
| 3 | Cysto-prostatitis | Micrococcus sporigenes | Eradicated | Cured |
| 4 | Chronic cysto-pyelitis | Enterobacter agglomerans | Eradicated | Cured |
| 5 | Cysto-prostatitis | Proteus rettgeri | Eradicated | Cured |
| 6 | Acute cystitis | Escherichia coli | Eradicated | Cured |
| 7 | Acute cystitis | Escherichia coli | Eradicated | Cured |
| 8 | Acute cystitis | Escherichia coli | Eradicated | Cured |
| 9 | Acute pyelonephritis | Escherichia coli | Eradicated | Cured |
| 10 | Acute cystitis | Proteus rettgeri | Eradicated | Cured |
| 11 | Acute cystitis | Klebsiella pneumoniae | Eradicated | Cured |
| 12 | Cysto-prostatitis | Pseudomonas aeruginosa | Persisted | Failure |
| 13 | Acute cystitis | Escherichia coli | Eradicated | Cured |

What is claimed is:

1. A pharmaceutical composition for treating bacterial infections of the urinary tract, comprising
    (a) an effective amount of trimethoprim,
    (b) an effective amount of, oxolinic acid or pharmaceutically acceptable salt thereof, and
    (c) an inert excepient therefor, the weight ratio of trimethoprim to oxolinic acid of 1:5.

2. A therapeutical method for treating a patient suffering from a bacterial infection of the urinary tract, which comprises administering to said patient
    (a) from 2 to 8 mg/kg/day of trimethoprim, and
    (b) from 10 to 40 mg/kg/day of oxolinic acid, in a weight ratio of trimethoprim to oxolinic acid of 1:5.

* * * * *